United States Patent [19]
Lee et al.

[11] Patent Number: 5,693,037
[45] Date of Patent: Dec. 2, 1997

[54] ABSORBENT ARTICLES HAVING IMPROVED SURFACTANT-TREATED HYDROPHILIC TOPSHEETS

[75] Inventors: Yann-Per Lee, Fairfield; Susan Nicole Lloyd, Middletown, both of Ohio

[73] Assignee: The Procter & Gamble Company, Cincinnati, Ohio

[21] Appl. No.: 426,337

[22] Filed: Apr. 21, 1995

[51] Int. Cl.[6] .................................................. A61F 13/15
[52] U.S. Cl. ........................ 604/381; 604/382; 604/378
[58] Field of Search ........................... 604/378, 385.1, 604/365, 367, 381, 382; 428/284–286, 290, 913

[56] References Cited

U.S. PATENT DOCUMENTS

| | | | |
|---|---|---|---|
| 4,077,410 | 3/1978 | Butterworth et al. | 128/287 |
| 4,323,069 | 4/1982 | Ahr et al. | 128/287 |
| 4,342,314 | 8/1982 | Radel et al. | 128/287 |
| 4,535,113 | 8/1985 | Foster et al. | 524/262 |
| 4,585,830 | 4/1986 | Sweet | 524/862 |
| 4,637,819 | 1/1987 | Ouellette et al. | 604/369 |
| 4,704,112 | 11/1987 | Suzuki et al. | 604/378 |
| 4,780,352 | 10/1988 | Palumbo | 428/138 |
| 4,798,603 | 1/1989 | Meyer et al. | 604/378 |
| 4,857,251 | 8/1989 | Nohr et al. | 264/103 |
| 4,920,168 | 4/1990 | Nohr et al. | 524/188 |
| 4,923,914 | 5/1990 | Nohr et al. | 524/99 |
| 5,019,062 | 5/1991 | Ryan et al. | 604/378 |
| 5,057,262 | 10/1991 | Nohr et al. | 264/211 |
| 5,057,361 | 10/1991 | Sayovitz et al. | 428/290 |
| 5,078,710 | 1/1992 | Suda et al. | 604/383 |
| 5,087,520 | 2/1992 | Suzuki et al. | 428/389 |
| 5,114,646 | 5/1992 | Nohr et al. | 264/103 |
| 5,120,888 | 6/1992 | Nohr et al. | 524/99 |
| 5,145,727 | 9/1992 | Potts et al. | 428/198 |
| 5,149,576 | 9/1992 | Potts et al. | 428/198 |
| 5,283,023 | 2/1994 | Nohr et al. | 264/103 |
| 5,300,358 | 4/1994 | Evers | 604/382 |
| 5,342,338 | 8/1994 | Roe | 604/383 |
| 5,352,217 | 10/1994 | Curro | 604/387 |
| 5,368,910 | 11/1994 | Langdon | 428/137 |
| 5,387,209 | 2/1995 | Yamamoto et al. | 604/384 |
| 5,397,824 | 3/1995 | Mcvie et al. | 524/265 |
| 5,413,655 | 5/1995 | Nohr et al. | 156/167 |
| 5,455,108 | 10/1995 | Quincy et al. | 428/266 |
| 5,478,335 | 12/1995 | Colbert | 604/383 |

FOREIGN PATENT DOCUMENTS

| | | | |
|---|---|---|---|
| 2079139 | 7/1993 | Canada . | |
| 2082445 | 7/1993 | Canada . | |
| 2081939 | 9/1993 | Canada . | |
| 0 325 543 A2 | 7/1989 | European Pat. Off. | D04H 1/54 |
| 0 165 807 | 8/1989 | European Pat. Off. . | |
| 0 338 393 | 10/1989 | European Pat. Off. . | |
| 0 523 719 A1 | 1/1993 | European Pat. Off. . | |
| 0 525 676 A2 | 2/1993 | European Pat. Off. | A61F 13/15 |
| 0 539 890 A1 | 5/1993 | European Pat. Off. . | |
| 0 596 223 A1 | 5/1994 | European Pat. Off. . | |

*Primary Examiner*—John G. Weiss
*Assistant Examiner*—David J. Cho
*Attorney, Agent, or Firm*—William Scott Andes; Roddy M. Bullock; E. Kelly Linman

[57] ABSTRACT

The present invention provides an absorbent article having a topsheet treated with a silicone-based surfactant to impart hydrophilicity. The absorbent article preferably includes a first, apertured, macroscopically expanded, three-dimensional, polymeric topsheet and preferably includes a second, apertured, macroscopically expanded, three-dimensional polymeric topsheet underlying the first topsheet. The multiple topsheets provide improved masking of bodily fluids absorbed and retained by the absorbent core. The first and second topsheets preferably include surfactants which impart hydrophilicity to differing degrees, and which preferably are selected from diverse surfactant categories. The use of a silicone-based surfactant imparts improved tactile qualities to the wearer-contacting surface of the first topsheet in comparison with non-silicone-based surfactants. These characteristics of the silicone-based surfactant provide improved dryness and cleanliness of appearance through low retention of fluid material at or near the surface of the topsheet itself and promoting fluid movement along the wetted surfaces and downward into the absorbent core.

24 Claims, 2 Drawing Sheets

FOREIGN PATENT DOCUMENTS

| | | |
|---|---|---|
| 0 596 532 A1 | 5/1994 | European Pat. Off. ......... A61F 13/46 |
| 0 597 224 A2 | 5/1994 | European Pat. Off. . |
| 0 598 204 A1 | 5/1994 | European Pat. Off. . |
| WO 92/18078 | 10/1992 | WIPO . |
| 9309741 | 5/1993 | WIPO . |
| WO 93/09741 | 5/1993 | WIPO . |
| WO 94/09066 | 4/1994 | WIPO . |
| 96/00548 | 1/1996 | WIPO ............................ A61F 13/15 |
| 96/00549 | 1/1996 | WIPO ............................ A61F 13/15 |

ABSORBENT ARTICLES HAVING IMPROVED SURFACTANT-TREATED HYDROPHILIC TOPSHEETS

FIELD OF THE INVENTION

The present invention relates to absorbent articles such as sanitary napkins, disposable diapers, adult incontinent briefs, and the like, and more particularly, the present invention relates to absorbent articles having topsheets treated with surfactants to impart hydrophilicity.

BACKGROUND OF THE INVENTION

It has long been known in the disposable absorbent bandage art that it is extremely desirable to construct absorptive devices such as disposable diapers, catmenial pads, sanitary napkins, incontinent briefs, and the like, which present a dry surface feel to the user to improve wearing comfort and to minimize the development of undesirable skin conditions due to prolonged exposure to moisture absorbed within the bandage.

One viable prior art solution to the aforementioned problem is disclosed in commonly assigned U.S. Pat. No. 4,342,314 issued to Radel, et al. on Aug. 3, 1982 and hereby incorporated herein by reference. Radel, et al. discloses an absorbent bandage with a wearer-contacting topsheet comprising a resilient, macroscopically expanded, three-dimensional plastic web exhibiting a combination of fiber-like and plastic properties. In a preferred embodiment, the macroscopically expanded, three-dimensional, plastic web topsheet disclosed in Radel, et al. exhibits a fine scale three-dimensional microstructure comprising a regulated continuum of capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel, et al. structure comprises an uppermost capillary opening or aperture formed by a multiplicity of fiber-like elements interconnected to one another in the uppermost plane of the web. Each of the fiber-like elements exhibits a substantially uniform U-shaped cross-section along its length. The cross-section of the fiber-like element comprises a base portion located in the wearer-contacting plane and a sidewall portion joined to each edge of the base portion, the sidewall portions extend generally in the direction of the absorbent pad-contacting surface of the web. The sidewall portions which intersect one another are joined to one another intermediate the wearing contacting surface and the absorbent pad contacting surface of the web, thereby forming a capillary network interconnecting the opposed surfaces of the web.

A topsheet of the type generally disclosed by Padel, et al. is highly effective in promoting rapid fluid transfer from the first, wearer-contacting surface to the second, absorbent pad-contacting surface of the topsheet. Accordingly, topsheets of this type have enjoyed widespread commercial success on catamenial pads due to their clean and dry appearance in use when contrasted to conventional non-woven fibrous topsheets. While an absorbent article having a topsheet of the type disclosed in Radel, et al. is highly effective in promoting rapid transfer of bodily fluids from the first, wearer-contacting surface to the second, absorbent pad-contacting surface, the degree of masking of bodily fluids, e.g., menses, retained within the absorbent core is dependent upon the size of the capillary networks. As the size of the capillary networks decrease the amount of masking provided by the topsheet increases. However, if the capillary networks are too small bodily fluids are not able to pass through the topsheet into the absorbent core thereby exposing the skin to moisture.

Accordingly, it is an object of the present invention to provide an absorbent article with a topsheet or multiple topsheets having superior fluid handling properties while providing increased masking of bodily fluids retained within the absorbent core.

SUMMARY OF THE INVENTION

The present invention pertains, in a preferred embodiment, to an absorbent article, e.g., sanitary napkin, pantiliner, diaper, adult incontinent brief, bandage, and the like having an improved topsheet rendered hydrophilic with a silicone-based surfactant. Preferably, the absorbent article comprises a first topsheet including a first apertured, macroscopically expanded, three-dimensional, polymeric web. The macroscopically expanded, three-dimensional, polymeric web has a body facing surface and a garment facing surface which are located in planes remote from one another. The absorbent article also preferably includes a second topsheet underlying the first topsheet. The second topsheet includes a second apertured, macroscopically expanded, three-dimensional, polymeric web having a body facing surface and a garment facing surface which are located in planes remote from one another. The absorbent article includes an absorbent core underlying the second topsheet. The absorbent core includes a body facing surface and a garment facing surface. The absorbent article also includes a backsheet underlying the absorbent core. The backsheet has a body facing surface and a garment facing surface.

In a preferred embodiment, the first and second topsheets include a continuum of interconnected, fiber-like elements forming a network of capillaries. To transmit fluids through the first and second topsheets and into the absorbent core, the apertures in the first topsheet are larger than the apertures in the second topsheet. In a particularly preferred embodiment, the apertures in the first topsheet are substantially non-aligned with the apertures in the second topsheet.

In a particularly preferred embodiment, the first and second topsheets are rendered hydrophilic to different degrees by treatment with different surfactants to provide superior fluid handling properties while providing increased masking of bodily fluids retained within the absorbent core.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify like elements, and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
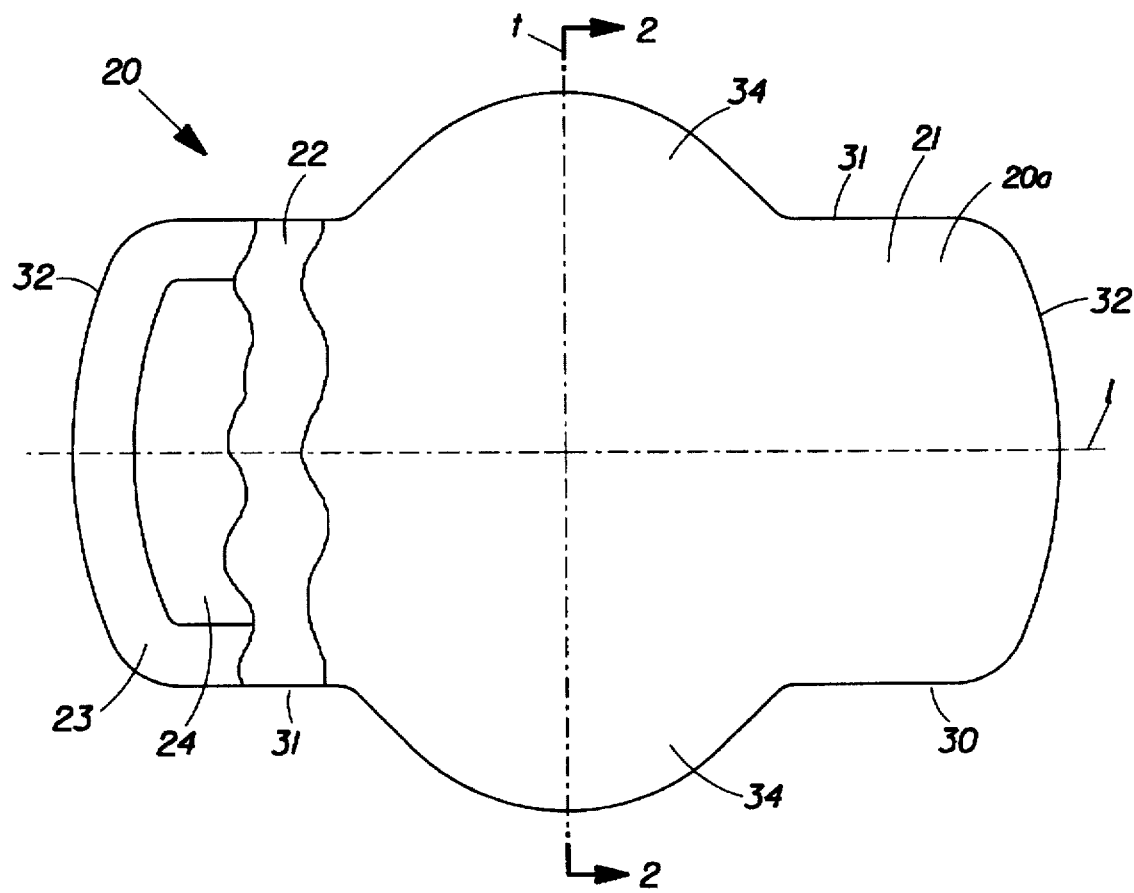
FIG. 1 is a top plan view of a sanitary napkin with portions cut-away to more clearly show the construction of the sanitary napkin.

A presently preferred embodiment of a unitary disposable absorbent article of the present invention is the catmenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catmenial pads such as pantiliners, or other absorbent articles such as diapers, incontinence briefs, and the like.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a first, fluid pervious topsheet 21, a second, fluid pervious topsheet 22, a fluid impervious backsheet 23 joined with topsheets 21 and 22, and an absorbent core 24 positioned between the second topsheet 22 and the backsheet 23.

The sanitary napkin 20 has two surfaces, a body-contacting surface or body facing surface 20a and a garment facing surface 20b. The sanitary napkin 20 is shown in FIG. 1 as viewed from its body facing surface 20a. The body facing surface 20a is intended to be worn adjacent to the body of the wearer while the garment facing surface 20b is on the opposite side and is intended to be placed adjacent to the wearer's undergarments when the sanitary napkin 20 is worn. The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

FIG. 1 shows a preferred embodiment of the sanitary napkin 20 in which the topsheets 21 and 22 and the backsheet 23 have length and width dimensions generally larger than those of the absorbent core 24. The topsheets 21 and 22 and the backsheet 23 extend beyond the edges of the absorbent core 24 to thereby form not only portions of the periphery but also side flaps.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
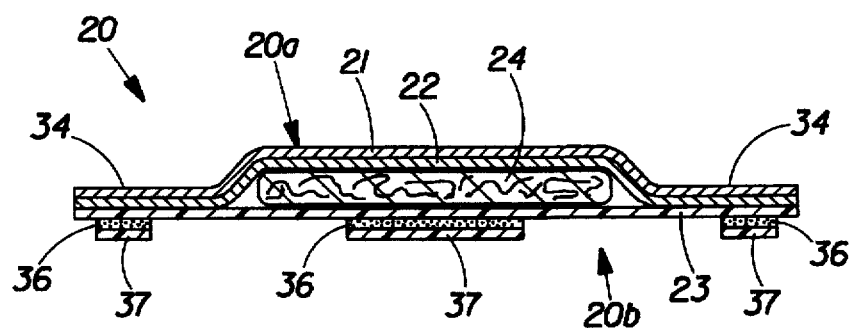
FIG. 2 is a cross-sectional view of the sanitary napkin of FIG. 1 taken along the section line 2—2.

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than a crotch portion of the undergarment prior to use.

The absorbent core 24 may be any absorbent means which is capable of absorbing or retaining liquids (e.g., menses and/or urine). As shown in FIG. 1, the absorbent core 24 has a body facing surface, a garment facing surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et at. Each of these patents are incorporated herein by reference.

The backsheet 23 and the second topsheet 22 are positioned adjacent the garment facing surface and the body facing surface, respectively, of the absorbent core 24 and are preferably joined thereto and to each other by attachment means (not shown) such as those well known in the art. For example, the backsheet 23 and/or the second topsheet 22 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., under the designation HL-1258, and by Findlay of Minneapolis, Minn., under the designation H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 has a body facing surface and a garment facing surface. The backsheet 23 is impervious to liquids (e.g., menses and/or urine) and is preferably as manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P181401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

The first and second topsheets, 21 and 22, are compliant, soft feeling, and non-irritating to the wearer's skin. Further, the topsheets are liquid pervious permitting liquids (e.g., menses and/or urine) to readily penetrate through their thickness. Suitable topsheets may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), or from a combination of natural and synthetic fibers.

Preferred topsheets comprise an apertured formed film. Apertured formed films are preferred for the topsheets because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; U.S. Pat. No. 4,637,819 issued to Ouellette, et al. on Jan. 20, 1987, and U.S. Pat. No. 5,006,394 issued to Baird on Apr. 9, 1991. Each of these patents are incorporated herein by reference. Other suitable formed films include hydroformed films such as those disclosed in U.S. Pat. No. 4,629,643, issued Dec. 16, 1986 to Curro et al., and U.S. Pat. No. 4,609,518, issued Sep. 2, 1986 to Curro, both of which are also hereby incorporated herein by reference. Preferred forms of hydroformed films would include those having microapertures formed therein. For some applications, it may be desirable to utilize a two-dimensional apertured film, particularly for the second topsheet, where visual and tactile impression are of lesser consequence.

In a preferred configuration, both the first and second topsheets are comprised of apertured formed films in a configuration such as that disclosed in U.S. Pat. No. 5,382, 217, issued to Curro on Oct. 4, 1994, which is hereby incorporated herein by reference. Alteratively, one or both of the topsheets may be comprised of a fluid-pervious non-woven web comprised of a synthetic fibrous material such as polypropylene, polyester, or polyethylene, natural fibers such as wood, cotton, or rayon, or combinations of natural and synthetic fibers, as well as various paper, tissue, or paper-like fibrous materials. Nonwoven webs may be apertured by techniques known in the art such as needle punching, hydroentangling, etc. One possible arrangement wherein a nonwoven web overlies a formed film web is disclosed in published PCT application WO 93/09741, entitled "Absorbent Article Having A Nonwoven and Apertured Film Coversheet", published May 27, 1993 naming Aziz et al. as inventors, which publication is hereby incorporated herein by reference.

Figure 3:
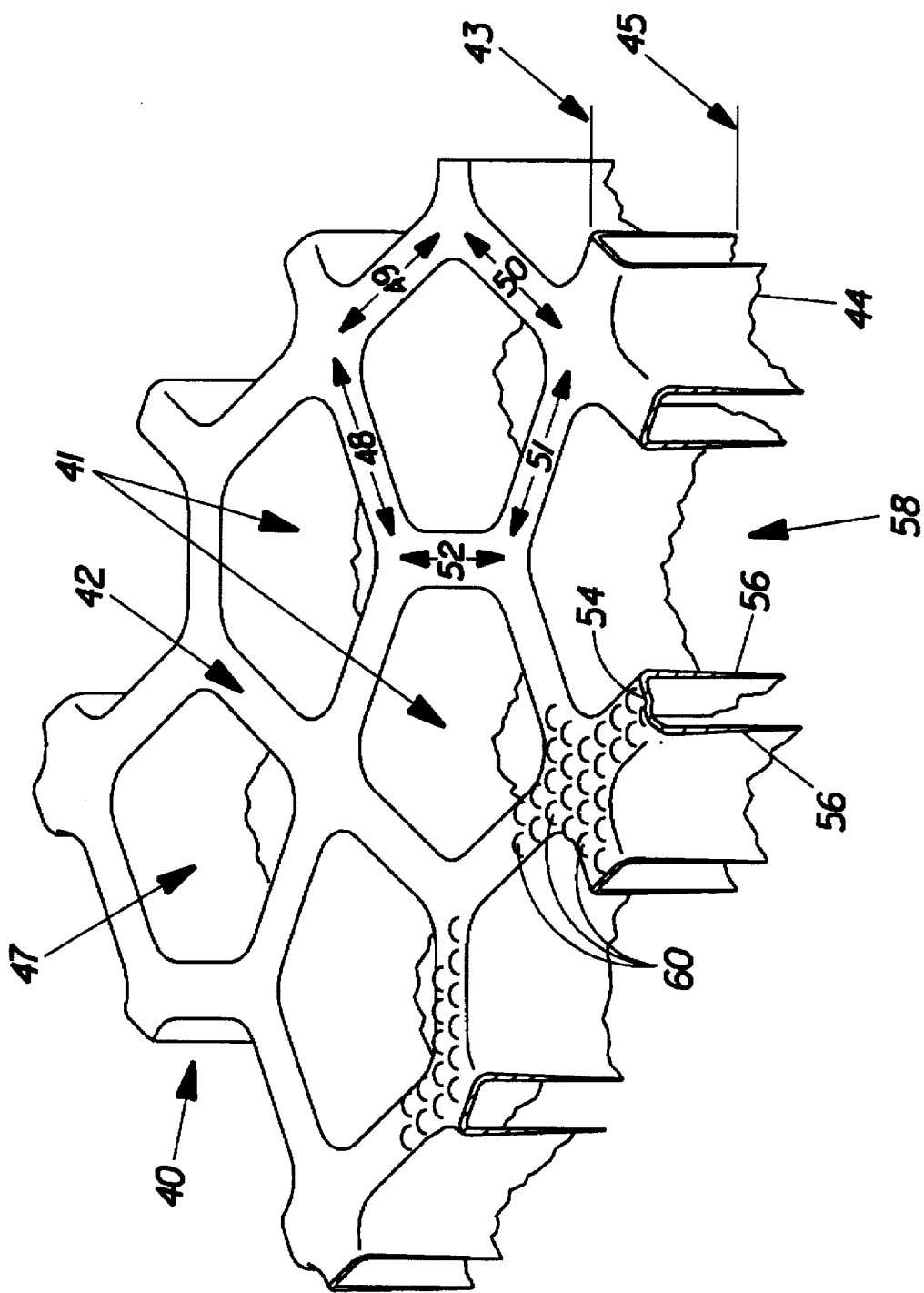
FIG. 3 is an enlarged, partially segmented, perspective illustration of a preferred fluid pervious web suitable for use as the first topsheet and the second topsheet of the present invention.

FIG. 3 is an enlarged, partially segmented, perspective illustration of a particularly preferred embodiment of an apertured, macroscopically expanded, three-dimensional, fiber-like, fluid pervious, polymeric web 40, generally in accordance with the teachings of commonly assigned U.S. Pat. No. 4,342,314 issued to Radel et al. on Aug. 3, 1982, which has been found suitable for use as the first topsheet 21 and the second topsheet 22 on sanitary napkin 20. The term "macroscopically expanded", when used to describe three-dimensional plastic webs of the present invention, refers to webs, ribbons and films which have been caused to conform to the surface of a three-dimensional forming structure so that both surfaces thereof exhibit a three-dimensional forming pattern of surface aberrations corresponding to the macroscopic cross-section of the forming structure, the surface aberrations comprising the pattern are individually discernible to the normal naked eye, i.e., a normal naked eye having 20/20 vision unaided by an instrument that changes the apparent size or distance of an object or otherwise alters the visual powers of the eye, when the perpendicular distance between the viewer's eye and the plane of the web is about 12 inches. The term "fiber-like", as utilized herein to describe the appearance of plastic webs of the present invention, refers generally to any fine scale pattern of apertures, random or non random, reticulated or non-reticulated, which connote an overall appearance and impression of a woven or nonwoven fibrous web when viewed by the human eye.

As can be seen in FIG. 3, the webs fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 41. The web 40 which exhibits a fiber-like appearance, embodies a three-dimensional microstructure extending from the webs uppermost, wearer-contacting or body facing surface 42 in plane 43 to its lowermost or garment facing surface 44 in plane 45 to promote rapid fluid transport from the uppermost surface 42 to the lowermost surface 44 of the web without lateral transmission of fluid between adjacent capillaries 41. As utilized herein, the term "microstructure" refers to a structure of such fine scale that its precise detail is readily perceived by the human eye only upon magnification by microscopic or other means well known in the art.

Apertures 47 in the body surface 42 are formed by a multiplicity of intersecting fiber-like elements, e.g., elements 48, 49, 50, 51, and 52, interconnected to one another in the body facing surface of the web. Each fiber-like element comprises a base portion, e.g., base portion 54, located in plane 43. Each base portion has a sidewall portion, e.g., sidewall portions 56, attached to each edge thereof. The sidewall portions 56 extend generally in the direction of the second surface 44 of the web. The intersecting sidewall portions of the fiber-like elements are interconnected to one another intermediate the first and second surfaces of the web and terminate substantially concurrently with one another in the plane 45 of the second surface.

In the particularly preferred embodiment shown in FIG. 3, the interconnected sidewall portions 56 terminate substantially concurrently with one another in the plane of the second surface 45 to form apertures 58 in the second surface 45 of the web. The network of capillaries 41 formed by the interconnected sidewall portions 56 between apertures 47 and 58 allows for free transfer of fluids from the body facing surface of the web directly to the garment facing surface of the web without lateral transmission of the fluid between adjacent capillaries.

The base portion 54 preferably includes a microscopic pattern of surface aberrations 60, generally in accordance with the teachings of commonly assigned U.S. Pat. No. 4,463,045 issued to Ahr et al. on Jul. 31, 1984. The microscopic pattern of surface aberrations 60 provide a substantially non-glossy visible surface when the web 40 is struck by incident light rays.

To increase the masking of bodily fluids retained in the absorbent core, the capillaries of the first topsheet 21 are preferably not of the same size, shape and/or in alignment with the capillaries of the underlying second topsheet 22. Accordingly, if the first and second topsheets are made from the same forming structure, thus creating similar topsheets, the first topsheet is preferably placed over the second topsheet such that the capillaries of the first and second topsheets are substantially non-aligned with one another. Alternatively, different forming structures can be used to form the first and second topsheets, respectively, such that they have different patterns, thus preventing alignment of the respective capillaries.

While non-alignment of the capillaries of the first topsheet 21 with those of the second topsheet 22 provides increased masking of bodily fluids retained by the absorbent core 24, bodily fluids must be allowed to transmit from the first topsheet 21 to and through the second topsheet 22 into the absorbent core 24. Therefore, the second topsheet cannot be sized, shaped or aligned such that it completely obstructs the apertures in the garment facing surface of the first topsheet 21. There must be a path for fluids to travel along between the first and second topsheets.

Preferably, the capillaries of the second topsheet 22 are slightly smaller in size than the capillaries of the first topsheet. By having the capillaries of the first topsheet 21 slightly larger than those of the second topsheet 22 a capillary gradient is created. The capillary gradient assists in the transmission of fluid deposited on the first topsheet 21, to and through the second topsheet 22 and into the absorbent core 24. It should be noted that with regard to apertured films or nonwovens, the terms "capillary" and "aperture" are used interchangeably herein as appropriate to refer to the defined openings in the material. While non-apertured nonwovens are not customarily thought of as having "apertures", they do in fact have an inter-fiber spacing which analogizes to the discussion herein with respect to the preferred apertured formed films.

In addition to preferably having a difference in aperture or capillary sizes between the first and second topsheets, it may be desirable to have multiple sizes of apertures or capillaries in any one topsheet. Particularly in the first topsheet, it may be desirable to include a pattern of larger apertures superimposed over a pattern of smaller apertures, such as is disclosed in European Patent Application 0,165,807, published Aug. 30, 1989, naming Osborn as inventor, which is hereby incorporated herein by reference. Regardless of aperture shapes, the aperture size may be described in terms of an equivalent hydraulic diameter, such as described in greater detail in the abovementioned Osborn published application. Accordingly, it may be desirable to have apertures of at least two different equivalent hydraulic diameters in the first and/or the second topsheets.

Whether or not the first and second topsheets have similar aperture structures, the first and second topsheets need not be of the same general caliper or thickness in the Z-direction. In the context of the present invention, the term "caliper" is utilized to describe the overall maximum dimension of the topsheet in the Z-direction, as distinguished from the gauge of the material utilized to form the topsheet. In a purely two-dimensional "flat" film, the two would be essentially equal, while in a macroscopically-expanded film as presently preferred the caliper of the topsheet would significantly exceed the gauge of the film.

Accordingly, it may be desirable to have the first topsheet of a larger caliper than the second topsheet, with second topsheets of comparatively small caliper providing a reduced travel distance between the absorbent core and the first topsheet and thus enhanced acquisition characteristics. Alternatively, it may be desirable for some applications to have the second topsheet of a larger caliper than the first. Of course, having both first and second top sheets of approximately equal caliper may also prove suitable for certain applications.

The first and second topsheets 21 and 22, may optionally be comprised of a multilayer polymeric film which exhibits an opaque appearance. Such a multilayer film includes a first outer layer comprised substantially of a polymeric material and a central filler-containing polymeric layer substantially continuously joined to one side of the first outer layer. The central filler-containing layer may include about 20 to 60 weight percent fillers relative to the filler-containing layer which are substantially uniformly dispersed therein. A filler such as titanium dioxide or carbonate may be used to give the topsheet a whitish, opaque appearance. The central filler-containing layer has a thickness from about 30 to about 70 percent of the total thickness of the multilayer fill. A second outer layer comprised substantially of a polymeric material has one side substantially continuously joined to the second side of the central filler-containing layer. The total multilayer film preferably has at least 20 weight percent filler relative to the total multilayer fill. A suitable example of such a multilayer topsheet is found in commonly assigned U.S. Pat. No. 5,261,899, issued Nov. 16, 1993 to Visscher and Perry, which is hereby incorporated herein by reference.

Preferred polymeric materials for the outer layers and the central filler-containing layer include polyolefins, particularly polyethylenes, polypropylenes and copolymers having at least one olefinic constituent. Other materials such as polyesters, nylons, copolymers thereof and combinations of any of the foregoing may also be suitable.

In accordance with the present invention, the body facing surfaces of the formed film topsheets are hydrophilic so as to help liquid to transfer through the topsheets faster than if the body facing surface was not hydrophilic so as to diminish the likelihood that menstrual fluid will flow off the topsheets rather than flowing into and being absorbed by the absorbent core. In a preferred embodiment, surfactant is incorporated into the polymeric materials of the first and second formed film topsheets such as is described in the above-referenced published PCT application WO 93/09741, entitled "Absorbent Article Having A Nonwoven and Apertured Film Coversheet", published May 27, 1993 naming Aziz et al. as inventors, incorporated herein by reference. Alternatively, the body facing surfaces of the topsheets can be made hydrophilic by treating them with a surfactant such as is described in the above referenced U.S. Pat. No. 4,950,254 issued to Osborn, incorporated herein by reference.

In a presently preferred configuration, the first topsheet is rendered hydrophilic with a silicone-based surfactant such as that commercially-available from Dow Corning, of Midland, Mich., under the trade designation DC 193. The surfactant may be incorporated into the starting material for the first topsheet (commonly known as "resin incorporated surfactant") or may be sprayed onto the surface of the topsheet either before joining with the second topsheet or afterward (in which case at least some of the sprayed surfactant will likely reach exposed surfaces of the second topsheet). In such a preferred configuration, the second topsheet is preferably also rendered hydrophilic, preferably with a non-silicone-based surfactant such as a hydrocarbon-based surfactant commercially available from ICI under the trade designations ATMER® 645 or ATMER® 100. Another suitable non-silicone-based surfactant is a hydrocarbon-based surfactant commercially available from Glyco Chemical, Inc. of Greenwich, Conn. under the trade name PEGOSPERSE® 200-ML. Silicone-based surfactants may also alternatively be employed in the second topsheet as well as the first topsheet. The surfactant is preferably incorporated into the starting material for the second topsheet as a "resin incorporated surfactant", although it could alternatively be sprayed onto the surface of the topsheet.

The use of a silicone-based surfactant has been found to impart improved tactile qualities to the wearer-contacting surface of the first topsheet in comparison with non-silicone-based surfactants. In addition, in a preferred configuration such as depicted in FIG. 1 wherein a second topsheet it interposed between the first topsheet and the absorbent core, the silicone-based surfactant imparts different surface chemistry and surface characteristics in comparison with the surface of the second topsheet. These characteristics of the silicone-based surfactant have been found to provide improved dryness and cleanliness of appearance through low retention of fluid material at or near the surface of the topsheet itself and promoting fluid movement along the wetted surfaces and downward into the absorbent core.

The surfactants utilized to impart hydrophilicity to the first and second topsheets are preferably selected for formulation and concentration so as to impart greater hydrophilicity to the second topsheet than the first topsheet. Said another way, the first and second topsheets preferably exhibit differing degrees of hydrophilicity. These differing degrees of hydrophilicity provide improved fluid acquisition, especially of small droplets of fluid on or near the surface of the topsheet, by establishing a hydrophilicity gradient and hence a driving force to move fluid downward into the absorbent core, while also improving rewet performance by resisting the movement of fluid back toward the first topsheet.

The first and second topsheets are preferably bonded to one another at least centrally so as to remain in intimate contact throughout the wearing of the absorbent article. Accordingly, one exemplary non-limiting bonding mechanism which has been found to be suitable is the use of a hot-melt adhesive applied in spiral fashion during the assembly process. Accordingly, the adhesive is applied to the body facing surface of the second topsheet and/or to the garment facing surface of the first topsheet before they are brought into contact.

The first and second topsheets may also be bonded by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258, and by Findlay of Minneapolis, Minn., under the designation H-2031. The attachment means will preferably comprise an open pattern network of filaments of adhesive as is disclosed in the above-referenced and incorporated U.S. Pat. No. 4,573,986 issued to Minetola, et al. on Mar. 4, 1986. An exemplary attachment means of an open pattern network of filaments comprises several lines of adhesive filaments swirled into a spiral pattern such as illustrated by the apparatus and method shown in the above-referenced patents which have been incorporated herein by reference: U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means in lines, points, or patterns as are known in the art. Under some circumstances and for certain applications it may also be desirable for the first and second topsheets to not be bonded to one another although oriented in overlying relation to one another.

Although much of the foregoing discussion has focused on the presently preferred configuration having superimposed first and second top sheets, it should be understood that the advantages of the present invention vis-à-vis the treatment of the first topsheet with a silicone-based surfactant are believed to be equally applicable to a configuration having a single topsheet. Accordingly, in a configuration similar to that of FIG. 1 the first topsheet 21 would directly overlie the absorbent core 24 and the first (and only) topsheet 21 would be joined directly to the backsheet 23. It should also be noted that the use of three or more superimposed topsheets is also to be encompassed by the present invention.

In other variations of the preferred configuration having first and second topsheets 21 and 22, the first and second topsheets need not be coextensive (i.e., they need not have the same overall size and/or shape). More particularly, while the first topsheet and the backsheet will typically generally define the overall size and shape of the absorbent article, the second topsheet may be smaller in lateral extent than the first topsheet in one or more directions. The second topsheet may therefore be sufficiently smaller than the first topsheet so as to be free of the peripheral bond joining the first topsheet and the backsheet.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

In a preferred embodiment of the present invention, the sanitary napkin 20 has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps 34 serve at least two purposes. First, the flaps 34 help serve to prevent soiling of the wearer's body and panties by menstrual fluid, preferably by forming a double wall barrier along the edges of the panty. Second, the flaps 34 are preferably provided with attachment means on their garment surface so that the flaps can be folded back under the panty and attached to the garment facing side of the panty. In this way, the flaps 34 serve to keep the sanitary napkin 20 properly positioned in the panty. The flaps 34 can be constructed of various materials including materials similar to the topsheet, backsheet, tissue, or combination of these materials. Further, the flaps 34 may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat. No. 4,608,047 issued to Mattingly on Aug. 26, 1986. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   (a) a first topsheet, said first topsheet including a first web having a body facing surface and a garment facing surface, said first topsheet including a silicone-based surfactant, such that said first topsheet exhibits a first degree of hydrophilicity to provide improved dryness and cleanliness appearance;
   (b) a second topsheet underlying said first topsheet, such that said second topsheet is between said first topsheet and an absorbent core, said second topsheet including a second web having a body facing surface and a garment facing surface, said second topsheet including a non-silicone-based surfactant, such that said second topsheet exhibits a second degree of hydrophilicity;
   (c) said absorbent core underlying said second topsheet, said absorbent core having a body facing surface and a garment facing surface; and
   (d) a backsheet underlying said absorbent core, said backsheet having a body facing surface and a garment facing surface.

2. The absorbent article of claim 1, wherein said first topsheet includes a continuum of interconnected, fiber-like elements forming a network of capillaries.

3. The absorbent article of claim 1, wherein said absorbent article is a sanitary napkin.

4. The absorbent article of claim 1, wherein said first topsheet includes apertures having at least two different equivalent hydraulic diameters.

5. The absorbent article of claim 1, wherein said silicone-based surfactant in said first topsheet is a resin-incorporated surfactant.

6. The absorbent article of claim 1, wherein said silicone-based surfactant in said first topsheet is a surface treatment.

7. The absorbent article of claim 1, wherein said first topsheet comprises an apertured, macroscopically expanded, three-dimensional, polymeric web.

8. The absorbent article of claim 1, wherein said first topsheet comprises a nonwoven web.

9. The absorbent article of claim 1, wherein said first topsheet comprises a microapertured hydroformed film.

10. The absorbent article of claim 1, wherein said second topsheet includes a continuum of interconnected fiber-like elements forming a network of capillaries.

11. The absorbent article of claim 1, wherein said second topsheet comprises an apertured, macroscopically expanded, three-dimensional, polymeric web.

12. The absorbent article of claim 1, wherein said second topsheet comprises a nonwoven web.

13. The absorbent article of claim 1, wherein said second degree of hydrophilicity exceeds said first degree of hydrophilicity.

14. The absorbent article of claim 1, wherein said non-silicone-based surfactant in said second topsheet is a resin-incorporated surfactant.

15. The absorbent article of claim 1, wherein said silicone-based surfactant in said first topsheet is a surface treatment and said non-silicone-based surfactant in said second topsheet is a resin-incorporated surfactant.

16. The absorbent article of claim 1, wherein said first topsheet comprises an apertured, macroscopically expanded, three-dimensional, polymeric web and said second topsheet comprises an apertured, macroscopically expanded, three-dimensional, polymeric web.

17. The absorbent article of claim 16, wherein the apertures in said first topsheet are larger than the apertures in said second topsheet.

18. The absorbent article of claim 16, wherein the apertures in said first topsheet are substantially non-aligned with the apertures in said second topsheet.

19. An absorbent article comprising:
  (a) a first topsheet, said first topsheet including a first apertured, macroscopically expanded, three-dimensional, polymeric web having a body facing surface and a garment facing surface, said first topsheet including a silicone-based surfactant, such that said first topsheet exhibits a first degree of hydrophilicity;
  (b) a second topsheet underlying and at least centrally secured to said first topsheet, said second topsheet including a second apertured, macroscopically expanded, three-dimensional, polymeric web having a body facing surface and a garment facing surface, said second topsheet including a non-silicone-based surfactant, such that said second topsheet exhibits a second degree of hydrophilicity;
  (c) an absorbent core underlying said second topsheet, said absorbent core having a body facing surface and a garment facing surface; and
  (d) a backsheet underlying said absorbent core, said backsheet having a body facing surface and a garment facing surface.

20. The absorbent article of claim 19, wherein said first topsheet includes a continuum of interconnected, fiber-like elements forming a network of capillaries.

21. The absorbent article of claim 19, wherein said second topsheet includes a continuum of interconnected fiber-like elements forming a network of capillaries.

22. The absorbent article of claim 19, wherein said absorbent article is a sanitary napkin.

23. The absorbent article of claim 19, wherein the apertures in said first topsheet are larger than the apertures in said second topsheet.

24. The absorbent article of claim 19, wherein said second degree of hydrophilicity exceeds said first degree of hydrophilicity.

* * * * *

UNITED STATES PATENT AND TRADEMARK OFFICE
CERTIFICATE OF CORRECTION

PATENT NO. : 5,693,037

DATED : December 2, 1997

INVENTOR(S) : YANN-PER LEE ET AL.

It is certified that error appears in the above-identified patent and that said Letters Patent is hereby corrected as shown below:

Column 1, line 15, "catmenial" should read -- catamenial --.

Column 1, line 55, "Padel," should read -- Radel, --.

Column 3, line 15, "catmenial" should read -- catamenial --.

Column 3, line 27, "catmenial" should read -- catamenial --.

Column 4, line 57, "at." should read -- al. --.

Column 5, line 23, delete "as".

Column 6, line 23, "Alteratively," should read -- Alternatively, --.

Column 8, line 30, "abovementioned" should read -- above-mentioned --.

Column 8, line 51, "Alteratively," should read -- Alternatively, --.

Column 8, line 53, "top sheets" should read -- topsheets --.

Column 9, line 1, "fill." should read -- film. --.

Column 9, line 6, "fill." should read -- film. --.

Column 9, line 36, "Coming." should read -- Corning --.

Column 10, line 57, "top sheets," should read -- topsheets, --.

Signed and Sealed this

Sixth Day of October, 1998

Attest:

BRUCE LEHMAN

Attesting Officer

Commissioner of Patents and Trademarks